US012708686B2

(12) United States Patent
Canady et al.

(10) Patent No.: US 12,708,686 B2
(45) Date of Patent: Aug. 18, 2026

(54) AIR FLOW TREATMENT SYSTEM AND METHOD FOR VENTILATION SYSTEMS

(71) Applicant: Jerome Canady Research Institute for Advanced Biological and Technological Sciences, Takoma Park, MD (US)

(72) Inventors: Jerome Canady, Lakeland, FL (US); Taisen Zhuang, Rockville, MD (US); Xiaoqian Cheng, Fairfax, VA (US); Saravana Murthy, Owings, MD (US)

(73) Assignee: Jerome Canady Research Institute for Advanced Biological and Technological Sciences, Takoma Park, MD (US)

( * ) Notice: Subject to any disclaimer, the term of this patent is extended or adjusted under 35 U.S.C. 154(b) by 625 days.

(21) Appl. No.: 17/927,290

(22) PCT Filed: May 24, 2021

(86) PCT No.: PCT/US2021/033938
§ 371 (c)(1),
(2) Date: Nov. 22, 2022

(87) PCT Pub. No.: WO2021/237219
PCT Pub. Date: Nov. 25, 2021

(65) Prior Publication Data

US 2023/0201392 A1 Jun. 29, 2023

Related U.S. Application Data

(60) Provisional application No. 63/028,957, filed on May 22, 2020.

(51) Int. Cl.
*A61L 2/14* (2006.01)
*A61L 2/26* (2006.01)
(Continued)

(52) U.S. Cl.
CPC *A61L 2/14* (2013.01); *A61L 2/26* (2013.01); *F24F 8/22* (2021.01); *H05H 1/246* (2021.05);
(Continued)

(58) Field of Classification Search
CPC .......... A61L 2/14; A61L 2/26; A61L 2202/11; A61L 2202/25; H05H 2245/15; H05H 2245/36; H05H 1/246
See application file for complete search history.

(56) References Cited

U.S. PATENT DOCUMENTS 8,334,422 B2 12/2012 Gutsol et al.
9,999,462 B2 6/2018 Canady et al.
(Continued)

FOREIGN PATENT DOCUMENTS

CN 101590272 A 12/2009
CN 104950087 A * 9/2015
(Continued)

OTHER PUBLICATIONS

Keidar M, Beilis II, “Plasma Engineering: application in aerospace, nanotechnology and bionanotechnology,” Oxford: Elsevier; 2013.
(Continued)

*Primary Examiner* — David E Smith
(74) *Attorney, Agent, or Firm* — 24IP Law Group USA, PLLC; Timothy R DeWitt

(57) ABSTRACT

A system and method for using cold atmospheric plasma to treat an air flow to inactivate viruses and sterilize the air flow. The system comprises a source of a carrier gas, a humidifier connected to said source of a carrier gas, a source of a feed gas, a plasma generator configured to plasmatize said carrier gas into a plasma; and a mixer having an interior chamber, an active electrode inside said interior chamber and connected to an electrical output of said plasma generator, an outer electrode connected to a ground and a
(Continued)

dielectric barrier between said inner electrode and said outer electrode, wherein said mixer has a first fluid input port connected to said source of a carrier gas, a second fluid input connected to said source of a feed gas and a fluid output connected to a ventilation system.

19 Claims, 12 Drawing Sheets

(51) Int. Cl.
*F24F 8/22* (2021.01)
*H05H 1/24* (2006.01)
*A61L 103/75* (2026.01)

(52) U.S. Cl.
CPC ........ *A61L 2103/75* (2026.01); *A61L 2202/11* (2013.01); *H05H 2245/15* (2021.05); *H05H 2245/36* (2021.05)

(56) References Cited

U.S. PATENT DOCUMENTS

| | | | | |
|---|---|---|---|---|
| 10,213,614 | B2 * | 2/2019 | Keidar | A61B 18/042 |
| 2004/0120845 | A1 * | 6/2004 | Potember | A61L 9/20 422/123 |
| 2012/0269677 | A1 | 10/2012 | Zhou et al. | |
| 2013/0319460 | A1 * | 12/2013 | Schneider | A61L 2/14 134/1.1 |
| 2016/0220714 | A1 * | 8/2016 | Weltmann | A61L 2/02 |
| 2019/0231411 | A1 * | 8/2019 | Canady | G16H 50/30 |
| 2019/0365483 | A1 | 12/2019 | Canady et al. | |
| 2020/0001628 | A1 | 1/2020 | Sumii et al. | |

FOREIGN PATENT DOCUMENTS

| | | | | |
|---|---|---|---|---|
| CN | 206481891 U | | 9/2017 | |
| CN | 108260269 A | * | 7/2018 | B01D 53/323 |
| ES | 2206203 T3 | | 5/2004 | |
| KR | 20100008095 | | 8/2010 | |
| WO | 2018191265 A1 | | 10/2018 | |
| WO | 2019199281 A1 | | 10/2019 | |

OTHER PUBLICATIONS

Chauvin, J., Judee, F., Yousfi, M. et al., “Analysis of reactive oxygen and nitrogen species generated in three liquid media by low temperature helium plasma jet,” Sci Rep 7, 4562 (2017).

M.Keidar, et al., “Cold plasma selectivity and the possibility of a paradigm shift in cancer therapy,” British Journal of Cancer (2011) 105(9), 1295-1301.

Yan D, Sherman J H and Keidar M, “Cold atmospheric plasma, a novel promising anticancer treatment modality,” Oncotarget. 8 15977-15995 (2017).

Keidar M, “Plasma for cancer treatment,” Plasma Sources Sci. Technol. 24 33001 (2015).

Hirst A M, Frame F M, Arya M, Maitland N J and O’Connell D, “Low temperature plasmas as emerging cancer therapeutics: the state of play and thoughts for the future,” Tumor Biol. 37 7021-7031 (2016).

Chernets N, Kurpad D S, Alexeev V, Rodrigues D B and Freeman T A, “Reaction chemistry generated by nanosecond pulsed dielectric barrier discharge treatment is responsible for the tumor eradication in the B16 melanoma mouse model,” Plasma Process. Polym. 12 1400-1409 (2015).

T. Xie, et al., “Inactivation of airborne viruses using a packed bed non-thermal plasma reactor,” J. Phys. Appl. Phys. 52 (2019).

J. Zimmerman, et al., “Effects of cold atmospheric plasmas on adenoviruses in solution,” J. Phys., D: 44 (2011) 505201.

X. Su et al., “Inactivation Efficacy of Nonthermal Plasma-Activated Solutions Against Newcastle Disease Virus,” Applied and Environmental Microbiology, May 2018, vol. 84, issue 9.

* cited by examiner

Patient
1192
1190
Endobronchial
Tube
CAP-generated
Species in the lungs
Major species
(aqueous):
H2O2, NO2-, NO3-,
ONOO-, O2-
Joint CAP Mixer
Major radicals (gas):
-OH, N2+, O
300
CAP Generator
1196
CAP
Connection
1194
Grounding Cable
200
1174
1176
Ventilator
Respiratory
Delivery System
1170
1198
1140b
Chamber
Humidity Meter
70%
Humidifier
1130c
MFC
1120
Air
1150
1160
Oxygen
1130b
Humidifier
MFC
1120
1140a
Chamber
Humidity Meter
70%
Humidifier
1142
1130a
MFC
MFC
1120
1120
1114
1112
Helium
1110

| Vital status | Baseline | During 1st part | After 1st part | During 2nd part | After 2nd Part |
|---|---|---|---|---|---|
| Time stamp | 8:00 | 8:43 | 8:47 | 8:52 | 8:56 |
| Body temp (C) | 33.7 | 34.5 | 35 | 35.2 | 35.3 |
| End tidal CO2 (mmHg) | 33 | 43 | 36 | 43 | 31 |
| O2 Saturation (%) | 100 | 98 | 99 | 97 | 100 |
| B.P. (mmHg) | 102/58 | 100/51 | 90/50 | 103/59 | 110/64 |
| pulse (Beats/min) | 87 | 92 | 83 | 87 | 94 |

FIG. 5A

| Vital status | During 3rd Part | After 3rd Part | During 4th Part | After 4th Part |
|---|---|---|---|---|
| Time stamp | 9:01 | 9:05 | 9:10 | 9:17 |
| Body temp (C) | 35.3 | 35.3 | 35.3 | 34.7 |
| End tidal CO2 (mmHg) | 22 | 27 | 29 | 28 |
| O2 Saturation (%) | 97 | 99 | 98 | 99 |
| B.P. (mmHg) | 97/54 | 103/51 | 94/50 | 100/52 |
| pulse (Beats/min) | 102 | 98 | 97 | 89 |

FIG. 5B

AIR FLOW TREATMENT SYSTEM AND METHOD FOR VENTILATION SYSTEMS

CROSS-REFERENCE TO RELATED APPLICATIONS

The present application claims the benefit of the filing date of U.S. Provisional Patent Application Ser. No. 63/028,957 filed by the present inventors on May 22, 2020.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for using cold atmospheric plasma to treat air flowing through a ventilation system such as a heating or air conditioning system.

Brief Description of the Related Art

Plasma medicine has qualified as a new scientific field after intense research effort in low-temperature or cold atmospheric plasma applications. Keidar M, Beilis II, "Plasma Engineering: application in aerospace, nanotechnology and bionanotechnology," Oxford: Elsevier; 2013. It is known that cold atmospheric plasmas ("CAP") produce various chemically reactive species including reactive oxygen species (ROS) and reactive nitrogen species (RNS). Chauvin, J., Judèe, F., Yousfi, M. et al., "Analysis of reactive oxygen and nitrogen species generated in three liquid media by low temperature helium plasma jet," *Sci Rep* 7, 4562 (2017). CAP is a cocktail containing ROS and RNS in combination with transient electric fields, UV and charged species.

CAP has already been proven to be effective in wound healing, skin diseases, hospital hygiene, sterilization, antifungal treatments, dental care, and cosmetics targeted cell/tissue removal. One of the most recent applications of CAP is in cancer therapy. M. Keidar, et al., "Cold plasma selectivity and the possibility of a paradigm shift in cancer therapy," British Journal of Cancer (2011) 105(9), 1295-1301. As a near-room temperature ionized gas, cold atmospheric plasma (CAP) has demonstrated its promising capability in cancer treatment by causing the selective death of cancer cells in vitro. See, Yan D, Sherman J H and Keidar M, "Cold atmospheric plasma, a novel promising anticancer treatment modality," *Oncotarget.* 8 15977-15995 (2017); Keidar M, "Plasma for cancer treatment," *Plasma Sources Sci. Technol.* 24 33001 (2015); Hirst A M, Frame F M, Arya M, Maitland N J and O'Connell D, "Low temperature plasmas as emerging cancer therapeutics: the state of play and thoughts for the future," *Tumor Biol.* 37 7021-7031 (2016). The CAP treatment on several subcutaneous xenograft tumors and melanoma in mice has also demonstrated its potential clinical application. See, Keidar M, Walk R, Shashurin A, Srinivasan P, Sandler A, Dasgupta S, Ravi R, Guerrero-Preston R and Trink B, "Cold plasma selectivity and the possibility of a paradigm shift in cancer therapy," *Br. J. Cancer.* 105 1295-301 (2011); Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," *Plasma Process. Polym.* 12 1400-1409 (2015).

Additionally, various systems have been disclosed and experiments have been performed in connection with the effect of CAP on viruses. U.S. Pat. No. 8,334,422 entitled "Method and Device for Air Disinfection and Sterilization, disclosed a method for decontaminating bioaeorsol with high concentrations of bacterial, viral, spore or other airborne microorganisms or biologic contaminants. In T. Xie, et al., "Inactivation of airborne viruses using a packed bed non-thermal plasma reactor," J. Phys. Appl. Phys. 52 (2019), the authors reported on their study of the effectiveness of a packed bed dielectric barrier discharge (DBD) NTP reactor to inactivate bacteriophage MS2 in aerosols. This work further was described in U.S. Published Patent Application No. 2020/0016286, entitled "Production of Immune-response Stimulating Aerosols by Non-thermal Plasma Treatment of Airborne Pathogens." In J. Zimmerman, et al., "Effects of cold atmospheric plasmas on adenoviruses in solution," J. Phys., D: 44 (2011) 505201, the authors reported successful inactivation of adenovirus, a non-enveloped double stranded DNA virus, in a solution using a surface micro-discharge technology operating in air. In X. Su et al., "Inactivation Efficacy of Nonthermal Plasma-Activated Solutions Against Newcastle Disease Virus," Applied and Environmental Microbiology, May 2018, vol. 84, issue 9, the authors reported on their investigation of the inactivation efficacy of Newcastle disease virus by non-thermal plasma-activated solutions.

Several different systems and methods for performing Cold Atmospheric Plasma (CAP) treatment have been disclosed. For example, U.S. Pat. No. 10,213,614 discloses a two-electrode system for CAP treatment of cancer cells.

Another exemplary Cold Atmospheric Plasma system is disclosed in U.S. Pat. No. 9,999,462. The disclosed system has two units, namely a Conversion Unit (CU) and a Cold Plasma Probe (CPP). The Conversion Unit is connected to high frequency electrosurgical generator (ESU) output and converts the ESU signal to a signal appropriate for performing cold atmospheric plasma procedures. The Cold Plasma Probe is connected to the Conversion Unit output. At the end of the Cold Plasma Probe cold plasma is produced and is thermally harmless to living tissue, i.e., it cannot cause burns to the tissue. This cold plasma, however, is deadly for cancer cells while leaving normal cells unaffected. The disclosed Cold Plasma Conversion Unit is unique in that it utilizes a high voltage transformer to up-convert the voltage (1.5-50 kV), down-convert the frequency (<300 kHz), and down-convert the power (<30 W) of the high-voltage output from an electrosurgical unit (U.S. Pat. No. 9,999,462).

Further, various systems and methods for controlling gas flow and an integrated gas-assisted electrosurgical generator having a graphical user interface is disclosed in WO2018/191265, entitled "Electrosurgical Gas Control Module" and WO2019199281, entitled "Gas Enhanced Electrosurgical Generator."

SUMMARY OF THE INVENTION

In a preferred embodiment, the present invention is a system and method for using cold atmospheric plasma to treat an air flow to inactivate viruses and sterilize the air flow. The system comprises a source of a carrier gas, a humidifier connected to said source of a carrier gas, a source of a feed gas, a plasma generator configured to plasmatize said carrier gas into a plasma; and a mixer having an interior chamber, an active electrode inside said interior chamber and connected to an electrical output of said plasma generator, an outer electrode connected to a ground and a dielectric barrier between said inner electrode and said outer electrode, wherein said mixer has a first fluid input port connected to said source of a carrier gas, a second fluid input connected to said source of a feed gas and a fluid output connected to a ventilation system. The system may further comprise a UV light array in said chamber of said mixer. The carrier gas and feed gas each may be air. The plasma generator may be configured to operate with a frequency in the range of 10 kHz to 200 kHz and an output peak voltage in the range of 3 kV to 6 kV. Still further, the plasma generator generates electrical energy having a frequency within 5 kHz of one of 40 kHz, 100 kHz and 200 kHz. The plasma generator comprises a high frequency electrosurgical generator and a low frequency converter.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 5A and 5B are tables of vital signs recorded during a swine model experience of a preferred embodiment of the present invention.

DETAILED DESCRIPTION OF THE PREFERRED EMBODIMENTS

Cold atmospheric-pressure plasma (CAP) generates numerous reactive oxygen species (ROS) and reactive nitrogen species (RNS), such as hydroxyl radical (·OH), singlet oxygen ($^1O_2$), nitrogen ion ($N_2^+$), atomic oxygen (O), as well as electrons, ions, and photons. Maximum concentration of these species can be reached with optimal amount of humidity in the gas. CAP-generated ROS and RNS can form hydrogen peroxide ($H_2O_2$), nitrite ($NO_2^-$), nitrate ($NO_3^-$), peroxynitrite (ONOO—) when interacting with biological fluid. Reactive species and radicals in the plasma phase (·OH, $N_2^+$, $^1O_2$, O) are short-lived species, whereas $H_2O_2$, $NO_2^-$, $NO_3^-$, and ONOO— in aqueous phase are long-lived species. The long-lived species will further interact with intracellular species and metabolic pathways, inducing cell apoptosis. The present invention provides a system and method with which a cold atmospheric plasma (non-thermal plasma) can be generated, and the reactive species sterilize a flow of air, for example, in a ventilation system.

Figure 1:
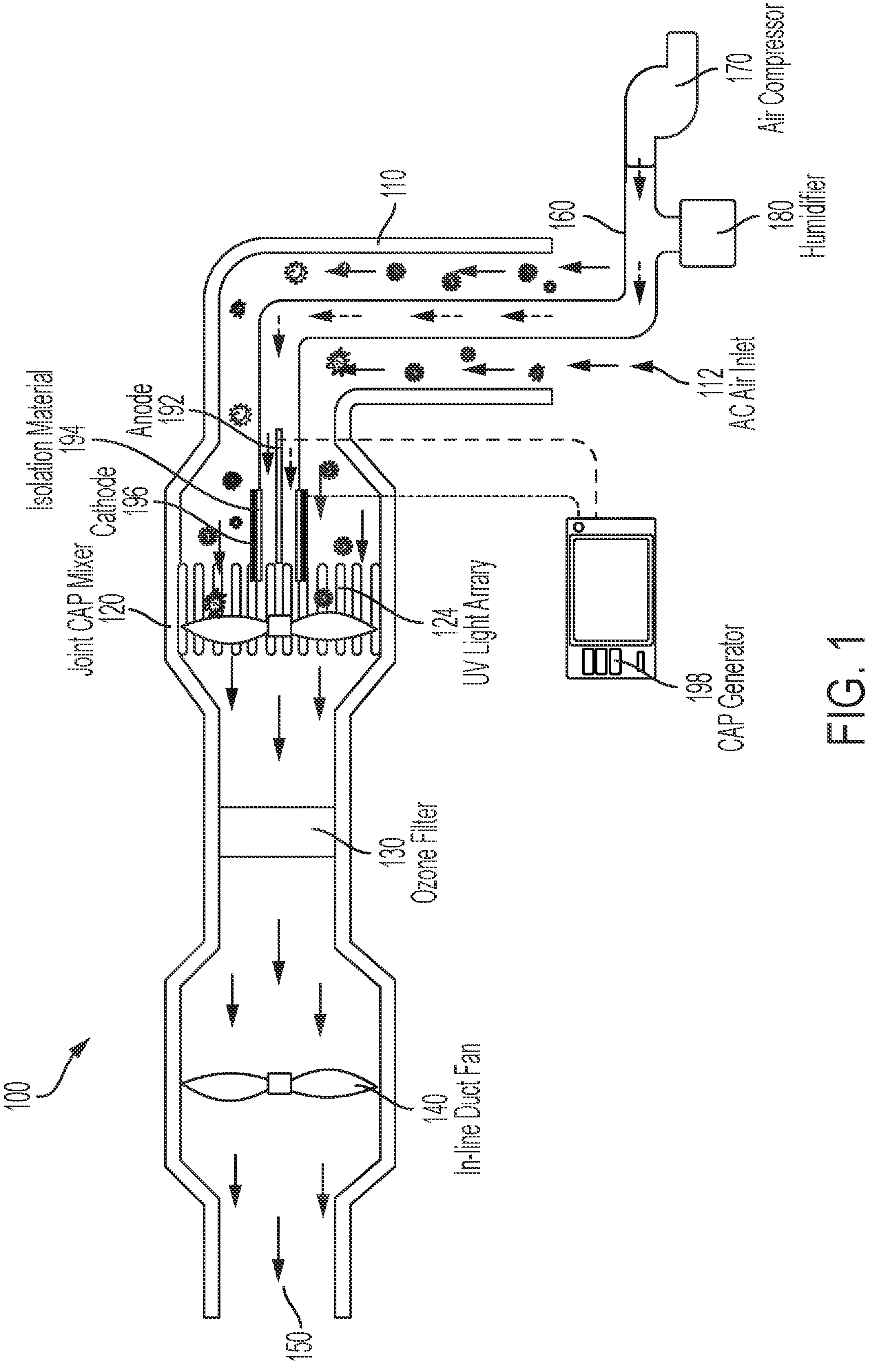
FIG. 1 is a diagram of a cold atmospheric plasma air treatment system in accordance with a preferred embodiment in which both a carrier gas and a feed gas are humidified.

A cold atmospheric plasma system 100 for sterilization of a flow of air is described with reference to FIG. 1. The system has a main ventilation tube 110, such as a heating or air conditioning vent, having an air inlet 112, a mixing section or CAP Joint Mixer 120, an ozone filter 130, an in-line duct fan 140, and an exit port 150. Within the main ventilation tube 110 is a secondary tube or channel 160 having an input connected to an air compressor 170 and an exit in the mixing section 120 of the main ventilation tube 110. A humidifier 180 for humidifying air flowing from the air compressor 170 in the secondary tube 160 is connected between the input and exit of the secondary tube or channel 160. At or near the exit of the secondary tube 160 is a dielectric barrier discharge assembly having a first electrode or anode 192 within a flow of air exiting the secondary tube 160 an isolation material or dielectric barrier or isolation material 194, and an outer ring electrode or cathode 196. The anode or active electrode 192 is connected to an electrical generator 198. In the mixing section 120 is an in-line fan 122 for mixing the plasma exiting the secondary tube or channel 160 with the air entering the CAP Joint Mixer from the air inlet 112, and a UV light array 124.

Figure 2:
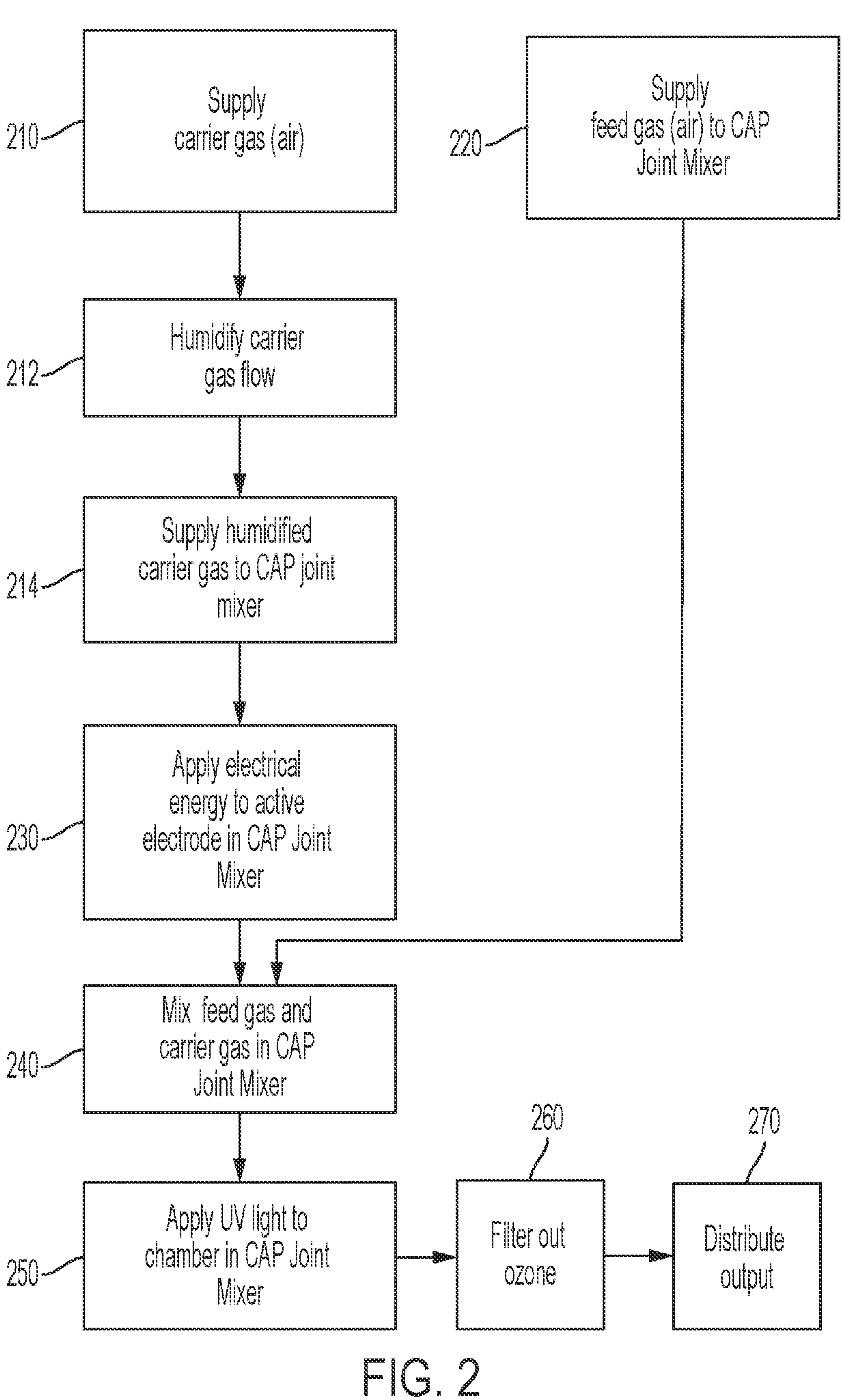
FIG. 2 is a flow diagram illustrating a method for t a cold atmospheric plasma air treatment system according to a preferred embodiment of the present invention.

A method for sterilization of an air flow according to a preferred embodiment of the present invention is described with reference to FIG. 2. A pressurized carrier gas (air), e.g., from a compressor 170, is supplied (step 210) to a humidifier 180. The pressurized air is humidified (step 212) in a humidifier 180. This humidified carrier gas is supplied (step 214) to a CAP Joint Mixer 120. At the same time, a feed gas (also air) is supplied (step 220) to the CAP Joint Mixer 120. Electrical energy is applied (step 230) to an inner electrode or anode 192 in the CAP joint mixer 120. UV light is applied (step 250) to the air mixing in the CAP Joint Mixer. The output of the CAP Joint Mixer is drawn or forced through an ozone filter 130 to remove ozone (step 260). The output is them distributed through the ventilation system.

In studies on the treatment of cancer using cold atmospheric plasma, it has been found that the CAP treatment decreases viability of cancer cells in a dose-dependent manner. Rowe, W., et al., "The Canady Helios Cold Plasma Scalpel Significantly Decreases Viability in Malignant Solid Tumor Cells in a Dose-Dependent Manner," Plasma, 2018. 1(1): p. 177-188.

Experiments

The cold atmospheric plasma system for where only the air was humidified was used to treat 1 mL phosphate buffer saline (PBS) in 12-well plates with the generator in Argon Coag Mode and Spray Mode operating at a frequency near 100 kHz for 3 min each. Voltage was set to be 70 V. Oxygen and air flow rate were both set to be 1 LPM. A mixture of oxygen ($O_2$) and air was humidified by bubbling through DI water. The relative humidity (RH) of the mixture is about 80%. Flow rate of helium, the carrier gas for cold atmospheric plasma (CAP), was set at 3 LPM. Therefore, the $O_2$ percentage of the final output gas from the endobronchial tube was about 24% in the $O_2$-air-He mixture.

Among of the cocktail of plasma-generated reactive oxygen species (ROS) and reactive nitrogen species (RNS) in the treated solution, hydrogen peroxide ($H_2O_2$) and nitrite ($NO_2^-$) are the most commonly studied long-lived species. Their concentrations were measured in treated phosphate-buffered saline (PBS) using Griess Reagent System (Promega, G2930) and colorimetric Hydrogen Peroxide Assay Kit (Sigma-Aldrich, MAK311-1KT) with CAP on or off. Results were read by a BioTek microplate reader at 550 nm and 595 nm for absorbance, respectively.

Electrosurgical generators typically have multiple modes of operation, including "cut" or cutting modes and "coag" or coagulation modes of operation. A cut mode typically will have a low voltage waveform form (e.g., 1 KV) with a high duty cycle, e.g., 100%. The coag mode of an electrosurgical generator typically creates a waveform with large amplitude but short duration "spikes" to achieve hemostasis (coagulation). For example, a coag mode on an electrosurgical generator may use a high voltage wave form at a 6% duty cycle. Different degrees of hemostasis (coagulation) can be achieved by utilizing varying degrees of "Blended" waveforms, e.g., 50% on/50% off, 40% on/60% off, or 25% on/75% off. Electrosurgical generators also have argon plasma coagulation modes, or "argon coag" modes. Argon Plasma Coagulation (APC) utilizes plasma produced by the ionization of a few millimeter diameter argon flow exhausting into ambient air from the electrosurgical handpiece. When compared to a cut mode, an argon coagulation mode on a generator may use a high voltage (e.g., 4 KV for argon coag versus 1 KV for a cut mode), less current (e.g., 200 mA for argon coag versus 500 mA for cut), and lower frequency (30 KHz for argon coag versus 390 KHz for cut). Electrosurgical generators also have a "Spray Mode," which is similar to the argon coag mode (similar voltage and current), but they have a random week of frequency, for example, from 10-30 KHz, which allows it to cover different tissue impedances.

Figure 3A:
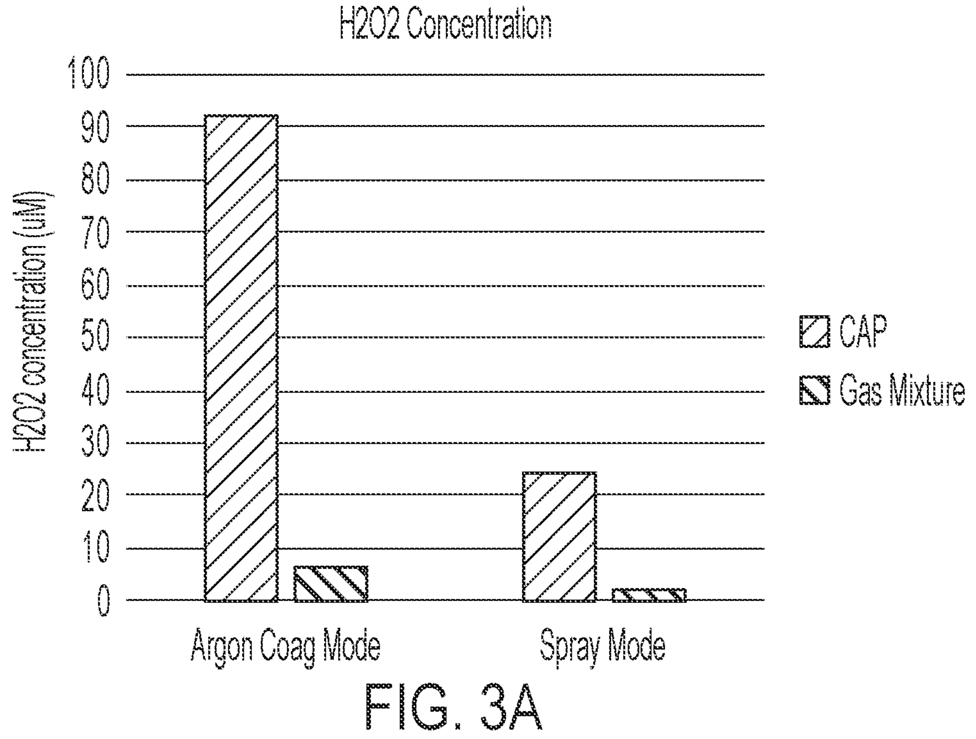
FIGS. 3A and 3B are graphs of the concentrations of $H_2O_2$ and $NO_2^-$ with a cold atmospheric plasma system for treatment of respiratory infections.
Figure 3B:
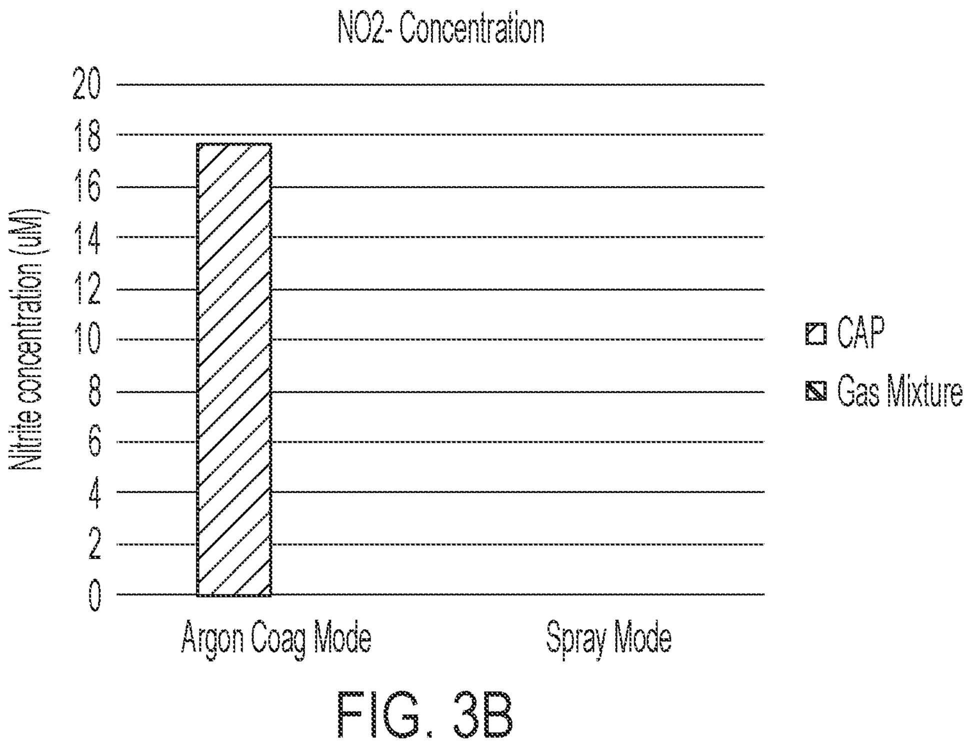

The concentrations of $H_2O_2$ and $NO_2^-$ with the present system treatment were plotted in FIGS. 3A and 3B. With CAP turned on, both species are higher when treated in Argon Coag Mode than when treated in Spray Mode. Gas-only treatment was also performed as a control. As indicated in FIGS. 3A and 3B, with 3 min of treatment, Argon Coag Mode at 70 V generated 90 μM $H_2O_2$ and 18 μM $NO_2^-$; whereas Spray Mode at 70 V generated 25 μM $H_2O_2$ and undetectable amount of $NO_2^-$. A gas mixture alone does not generate significant amount of ROS or RNS.

CAP Plasma Validation

Cold atmospheric plasma has been reported to induce inactivation of airborne viruses (Xia, T., et al., *Inactivation of airborne viruses using a packed bed non-thermal plasma reactor*. Journal of Physics D: Applied Physics, 2019. 52(25)), deactivation of hepatitis B virus while keeping normal liver function during CAP treatment (Shi, X.-M., et al., *Effect of Low-Temperature Plasma on Deactivation of Hepatitis B Virus*. IEEE Transactions on Plasma Science, 2012. 40(10): p. 2711-2716), inhibition of HIV replication (Volotskova, O., et al., *Cold Atmospheric Plasma Inhibits HIV-1 Replication in Macrophages by Targeting Both the Virus and the Cells*. PLoS One, 2016. 11(10): p. e0165322), inactivation of Newcastle disease virus and avian influenza virus without destruction of the antigenic determinants for vaccine preparation (Wang, G., et al., *Non-thermal plasma for inactivated-vaccine preparation. Vaccine,* 2016. 34(8): p. 1126-32) and so forth. In this study, CAP is combined with a ventilator system to achieve the delivery of CAP as well as the treatment of the virus throughout the patient's respiratory system.

Wu el al (Wu, Y., et al., *MS2 virus inactivation by atmospheric pressure cold plasma using different gas carriers and power levels*. Appl Environ Microbiol, 2015. 81(3): p. 996-1002) suggested that the ambient air as carrier gas produced the highest level of inactivation at power levels of 20 and 24 W, followed by the gas carriers Ar—$O_2$ (2%, vol/vol) and He—$O_2$ (2%, vol/vol). In addition, air is a required input gas for all ventilators. Hence air as carrier gas is the best option for a CAP-equipped ventilator. Relative humidity (RH) as an important factor of the air will be studied for an optimal configuration in addition to CAP treatment parameters including discharge voltage (V) and treatment time (t).

CAP-Generated Reactive Species

Reactive species generated by CAP can be confirmed within the plasma beam using optical emission spectroscopy (OES) and in aqueous solution by kits based on species.

Reactive Species in the Plasma Beam

An optical emission spectrometer (Ocean Optics HR2000) is used to detect the species in the plasma beam in the range of 200-900 nm. The plasma emissions are collected in a direction perpendicular to the plasma beam axis and at 1-mm increments in axial direction using a collimating lens. The plasma emission is transmitted to the spectrometer via optical fiber.

Reactive Species in the Solution

Kondeti et al did a thorough research on the species generated in CAP-treated saline and water based on their half-lives. Kondeti, V., et al., *Long-lived and short-lived reactive species produced by a cold atmospheric pressure plasma jet for the inactivation of Pseudomonas aeruginosa and Staphylococcus aureus*. Free Radic Biol Med, 2018. 124: p. 275-287. They concluded that long-lived species played a dominant role when the plasma was not in direct contact with the saline; whereas short-lived species was more important when the plasma touched the liquid. Long-lived species in CAP-treated solution like $NO_2^-$ and $H_2O_2$ concentrations can be measured in air flow-treated phosphate buffer saline (PBS) using Griess Reagent System (Promega, G2930) and Fluorimetric Hydrogen Peroxide Assay Kit (Sigma-Aldrich, MAK165-1KT) with CAP on or off. Results will be read by a BioTek microplate reader at 540 nm for absorbance and 540/590 nm for fluorescence, respectively.

Ozone can be a concern for CAP-based ventilator because it can have detrimental impacts on human health. Ozone concentration should be measured at the exhaust of the ventilator and reduced with filters to meet the air quality standards.

CAP Effect on the Cells

Lung cancer cell line A549 will be used for the efficacy of CAP treatment. Air flow-only treatment will be used as control group. The viability of the cells will be evaluated by 3-(4,5-dimethylthiazol-2-yl)-2,5-diphenyl tetrazolium bromide (MTT) assay.

In conclusion, with tuned configuration, CAP-based ventilators could benefit patients with respiratory diseases like pneumonia, COVID19, or lung cancer.

CAP Plasma Virus Inactivation Validation

Respiratory disease-causing viruses such as COVID-19 and severe acute respiratory syndrome (SARS) are transmitted by aerosolized droplets containing the infection virus. Cold atmospheric-pressure plasma (CAP) generates numerous reactive oxygen species (ROS) and reactive nitrogen species (RNS), such as hydrogen peroxide ($H_2O_2$), singlet oxygen ($^1O2$), ozone (O3), nitric oxide (·NO), and hydroxyl radical (·OH), as well as electrons, ions, and photons, in which ·OH, $^1O_2$, ·NO, $O_2$·—, ·$NO_2$, and ONOO— are short-lived species whereas $H_2O_2$, $NO_2$—, and $NO_3$—, are long-lived species. Various studies have shown that the CAP could inactivate viruses and other microbes. The potential inactivation mechanisms of the virus by the CAP are by inducing to high oxidation-reduction potential (ORP) and electrical conductivity by producing large number of free radicals. The reactive oxygen and nitrogen species could react with carbohydrates and initiate lipid peroxidation and cross-linking of the fatty acid side chains, resulting in alterations of the chemical bonds and molecular structure. They induce oxidative stress by causing protein peroxidation and inducing the destruction of the virus envelope, singlet oxygen could rapidly react with cysteine to generate the major product of cystine (R-cys-S-S-cys-R) with disulfides, they selectively reacted with tyrosine, tryptophan, and histidine to produce hydroperoxides resulting in protein aggregation and ultimately resulting in changes to the viral morphology. Moreover, they can damage viral nucleic acids encoding enzymes, by oxidizing guanine and induce cross-links between guanine and lysine contributing to reduced gene expression and the elimination of virus replication, thereby leading to virus inactivation. The cold plasma system of the present invention generates ionized cold plasma in a humidified setup to produce reactive species that are fed to virus infected patient via endobronchial tube. The output of the system contains reactive oxygen species (ROS) and reactive nitrogen species (RNS) which would inactivate the virus present in the patient's bronchial cells.

Human epithelial lung carcinoma cell line A549 (ATCC, CCL-185) was used to study the efficacy of the present invention. A549 cells were seeded at a density of $10^5$/well in 12-well plates and treated for up to 17 minutes. The frequency was near 100 kHz. Voltage was set to be 70 V. Flow rate of helium, the carrier gas for cold atmospheric plasma (CAP), was set at 3 LPM. The total flow rate of oxygen ($O_2$) and air were set to be 2 LPM. The $O_2$ percentage of the final output gas from the endotracheal tube was about 16, 24, and 32% in the $O_2$-air-He mixture.

The feed gas of $O_2$ and air mixture or He was humidified by bubbling through DI water. The relative humidity (RH) of the humidified gas was measured constantly with a humidity sensor.

Thiazolyl blue tetrazolium bromide (MTT) was purchased from Sigma-Aldrich (St. Louis, MO, USA) and viability assays were carried out 48 hours after CAP treatment according to the manufacturer's protocol. Results were read by a BioTek microplate reader at 570 nm for absorbance.

Figure 3C:
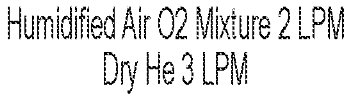
FIG. 3C is a graph of viability of A549 cells treated with a cold atmospheric plasma system with humidified $O_2$ and air mixture and various $O_2$ percentage for up to 4 minutes.
Figure 3C:
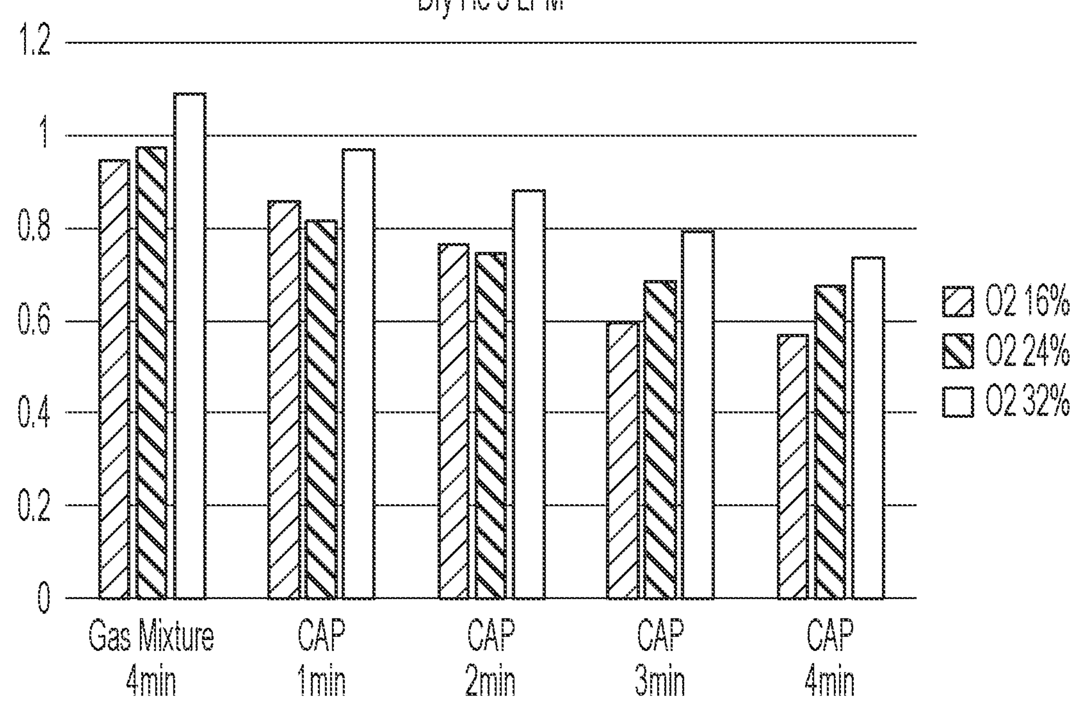
Figure 3D:
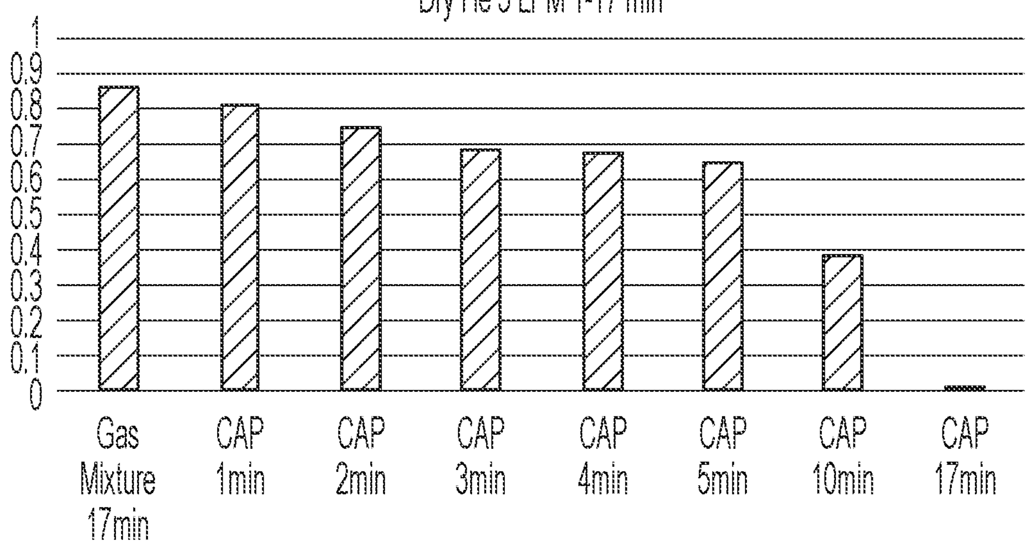
FIG. 3D is a graph of viability of A549 cells treated by a cold atmospheric plasma system with humidified Air/$O_2$ mixture and dry He with 24% $O_2$ for up to 17 minutes.
Figure 3E:
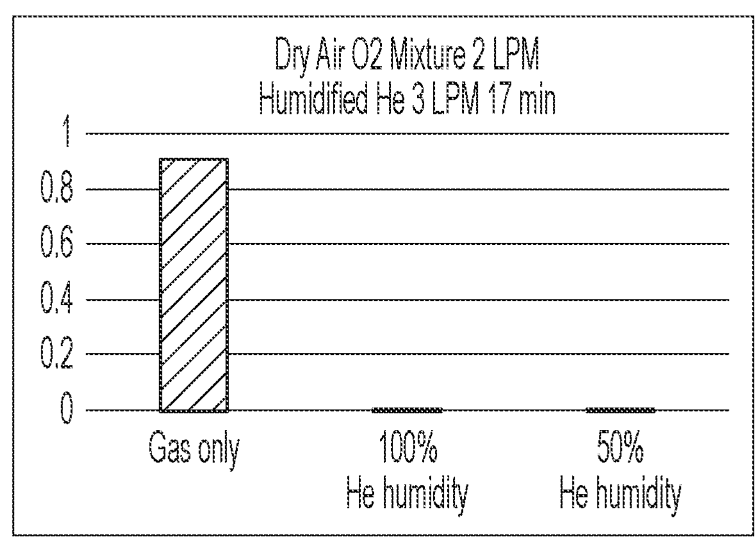
FIG. 3E is a graph of viability of A549 cells treated by a cold atmospheric plasma system with humidified helium and dry $O_2$ and air mixture (with 24% $O_2$) for 17 minutes.
Figure 3F:
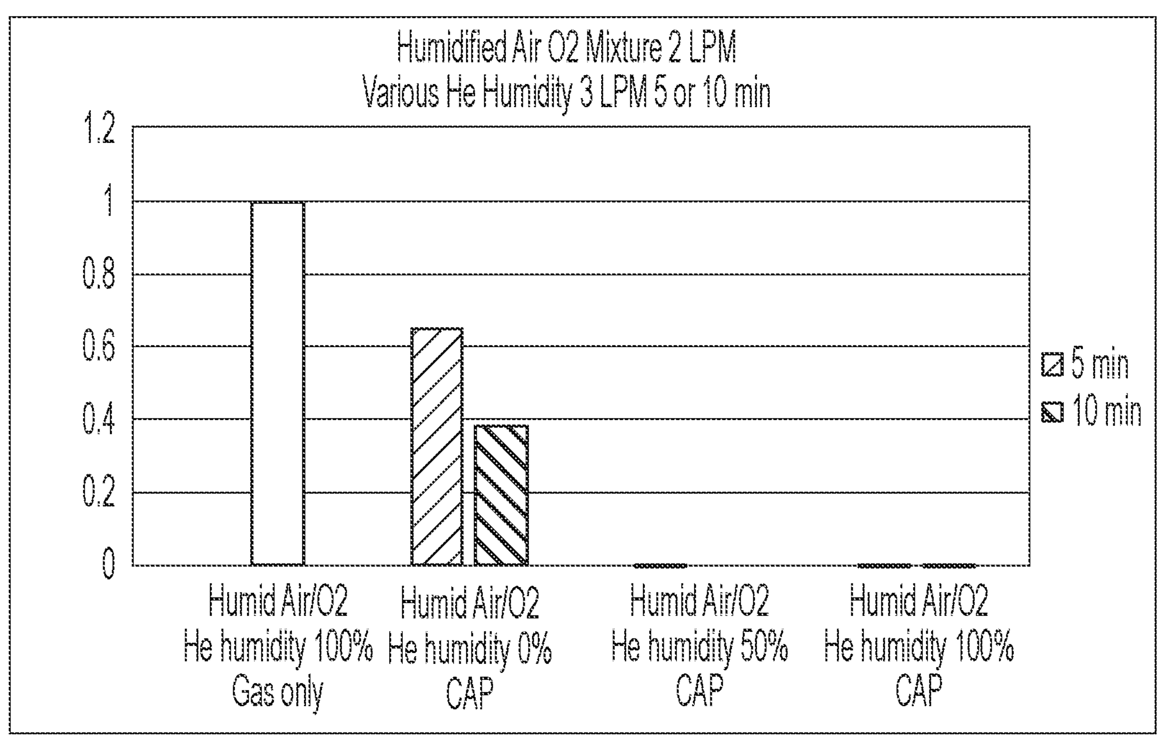
FIG. 3F is a graph of viability of A549 cells treated by a cold atmospheric plasma system for 5 or 10 minutes with humidified Air/$O_2$ mixture (with 24% $O_2$) and various helium humidity.

The viability of A549 cells treated by the present invention were plotted, as shown in FIGS. 3C-3E. FIG. 3C shows the viability of A549 cells treated by the setup of the present invention with air mixture humidity adjustment for up to 4 minutes. The viability of A549 cells was decreased gradually with increasing treatment time. With 4 min of treatment, the viability was reduced to 60% (compared to no treatment). Oxygen fraction increasing in the gas mixture has indicated a weakened effect of the treatment from the FIG. 3C.

The same setup with 24% $O_2$ in the feeding gas was then used to treat the cells for up to 17 min (FIG. 3D). Cell viability was reduced below 40% after 10 min of treatment compared to no treatment, and the cells were completely eliminated after 17 min of treatment.

When treated with the setup where only the helium is humidified, with helium humidity adjustment for 17 min, all the cancer cells were eliminated by the CAP treatment as well (data shown in FIG. 3E).

Effect of Treatment with Humidified Air/O2 Mixture and Humidified Helium

A549 cells were treated with 100% humidified Air/$O_2$ mixture (1:1 v/v) at a flow rate of 2 LPM ($O_2$ fraction 24%). Helium flow rate was 3 LPM and humidity was set at 0%, 50%, and 100%.

A549 cells without treatment attached firmly to the culture dish, and nuclei were intact. The control in this experiment was Air/$O_2$ and He mixture-treated for 10 min. Cells did not demonstrate any morphological changes compared to no treatment.

When He humidity was set at 0% (dry helium), the cells started to shrink within 5 min of cold plasma system treatment, but a significant amount of the cells were still viable. After increasing the treatment time to 10 min, cell death was identified.

When He humidity was increased to 50%, at 5 min of treatment time, the cells demonstrated shrinkage and blebbing of the membrane. Cell shrinkage was more severe at 10 min treatment time, and dead cells were visualized in a floating pattern.

When He humidity was increased to 100% at 5 or 10 min of treatment, almost all the cells were fragmented and not viable.

MTT viability assay was performed on the cells. He humidity at 0% (dry helium) and 5 min treatment time reduced the viability to 60%, and at 10 min the viability was reduced the viability to 40% compared to no treatment. When He humidity was set to 50% or 100%, there were no viable cells at 5 or 10 min of treatment.

Swine Model

The present invention was tested on a female swine at Medical Innovation & Training Institute (Henderson, NV). The weight of the swine was 55 kg, and the length was 4'2". A total of 15 min treatment at 40 V was administered in 4+4+4+3 min manner with 5 min break between each interval. Voltage was set at 40 V. Flow rate of helium was set at 3 LPM. Oxygen flow rate was 3 LPM.

Blood samples were collected in 10 mL K2EDTA tubes immediately. Blood in EDTA tubes was stored on ice and brought back to JCRI-ABTS for immediate processing. Lung tissue was collected after the treatment and placed immediately in 10% formalin. Tissue morphology is determined by hematoxylin staining to check the damage of the lung tissue after CHCPHS treatment.

Serum concentrations of IL-6, TNF-α, CRP, Angiopoietin-1, IL-1b & IL-10 were determined in triplicates with a commercial ELISA for porcine IL-10 (Quantikine Porcine Immunoassays, R&D Systems, USA) according to the manufacturer's instructions. The minimum limits of detection were as follows: IL-1β 10 pg mL-1; IL-6 10 pg mL-1; IL-10 1.8 pg mL-1; TNF-α 2.8 pg mL-1 and IFN-γ 2.7 pg mL-1.

Samples of decellularized lung and trachea were analyzed with light microscopy and compared with native, untreated cross-sections. Tissue samples were fixed in 10% formalin, embedded in paraffin and sectioned following standard protocols. We cut tissue into 5-10 μm sections, hematoxylin and eosin (H&E) to determine if remnant nuclear structures could be observed after decellularization as compared with controls. The sections were analyzed by routine bright field and fluorescence microscopy (Carl Zeiss, Germany). Images were acquired with the Zeiss Imaging System.

All values in the figures and text are shown as mean±SEM. A two-tailed Student's t-test was performed, considering P values less than 0.05 as statistically significant. The commercially available Microsoft Excel was used for data analysis.

Experimental Setup

Figure 4:
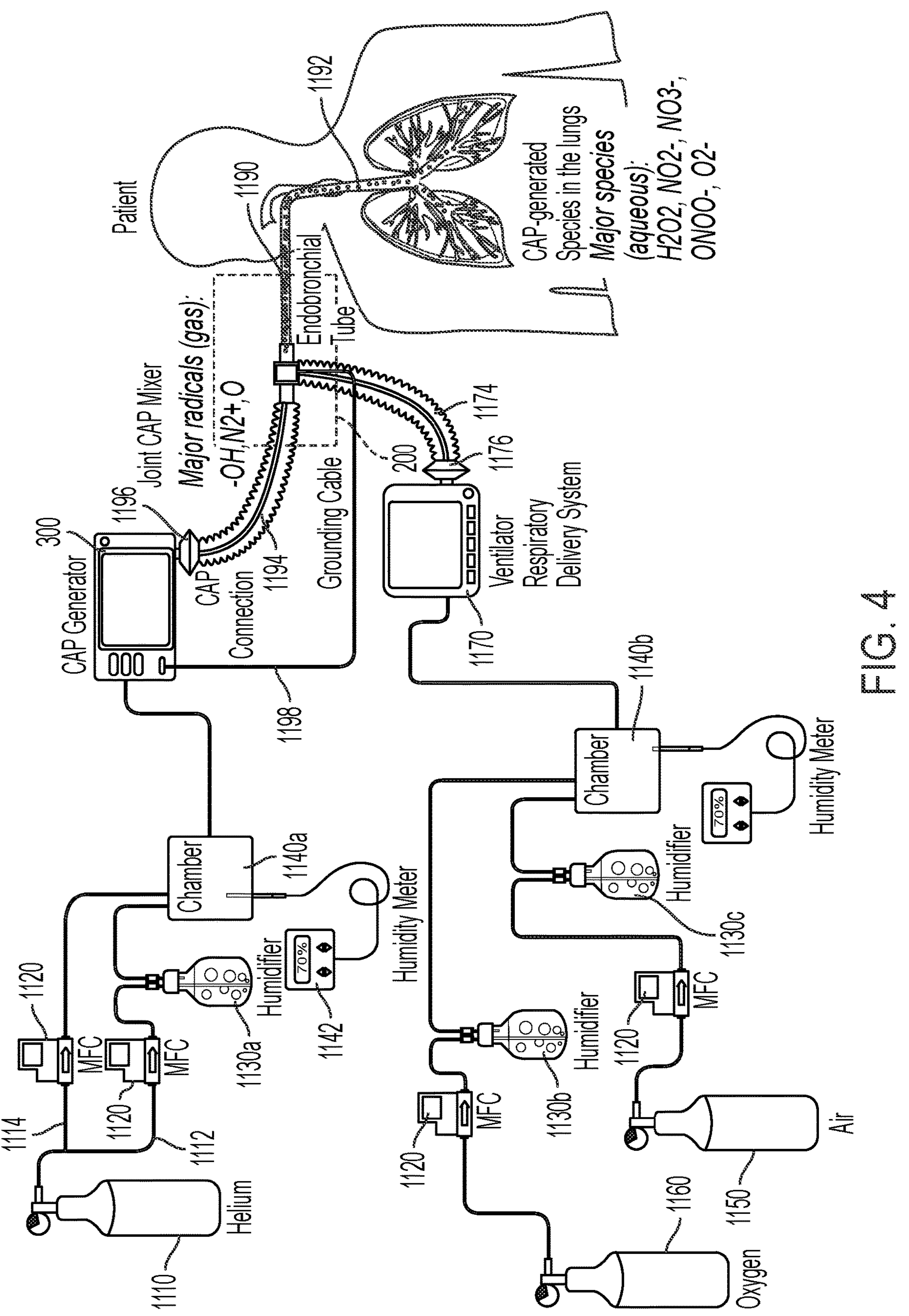
FIG. 4 is a diagram of an experimental setup for an experiment demonstrating the safety of the present invention.
Figure 6A:
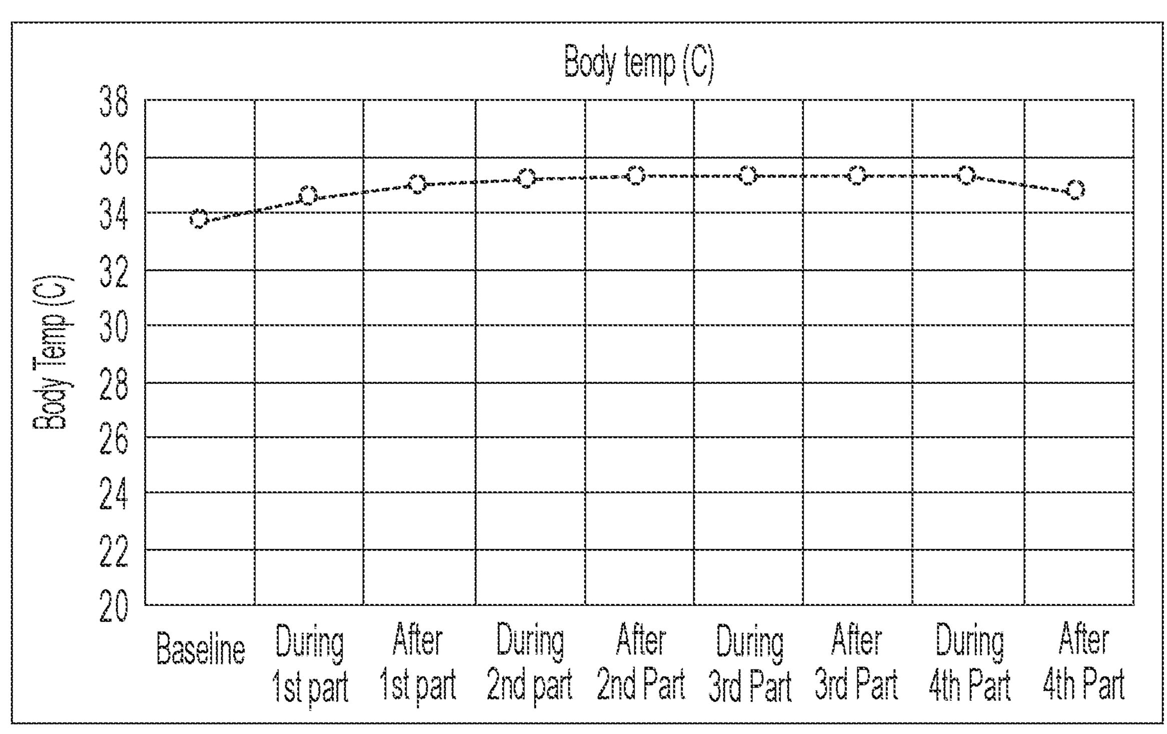
FIGS. 6A and 6D are graphs of the data in the tables of FIGS. 4A and 4B.
Figure 6B:
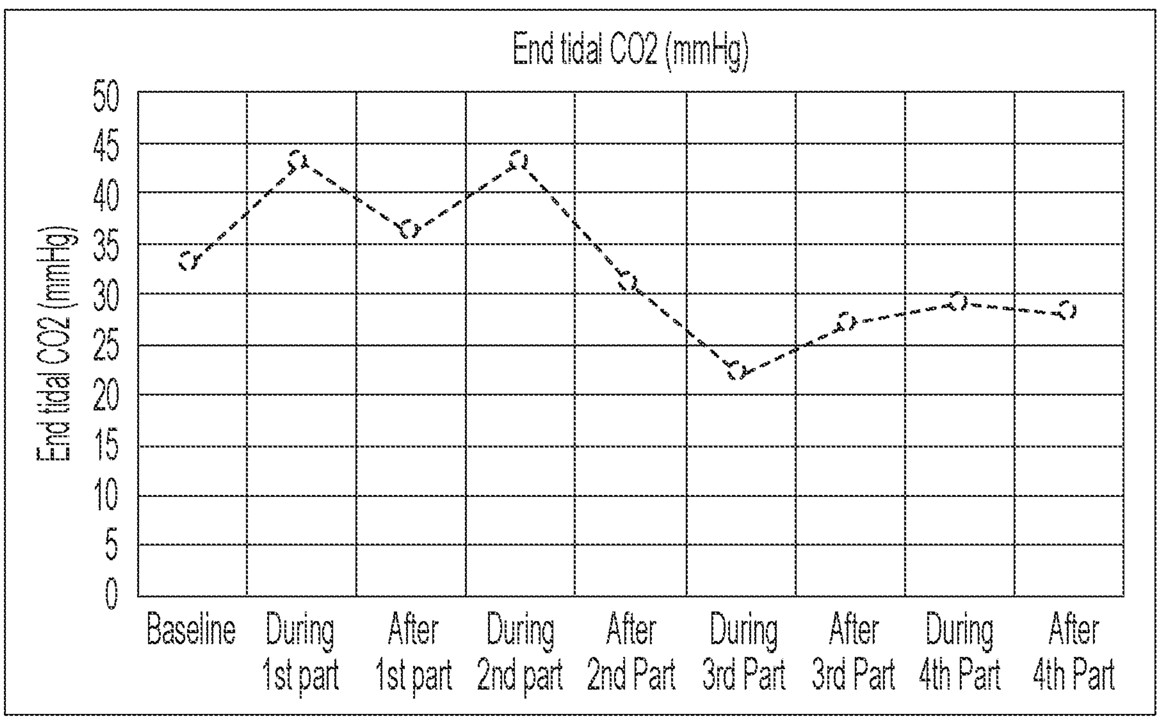
Figure 6C:
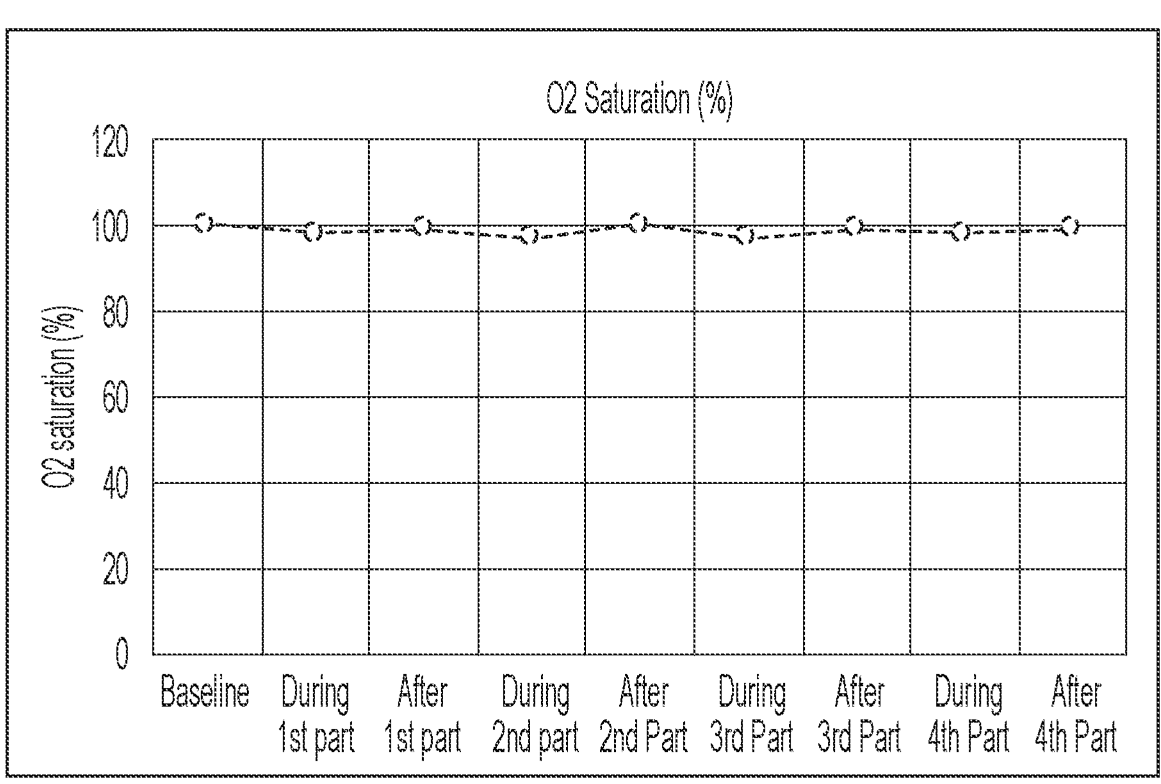
Figure 6D:
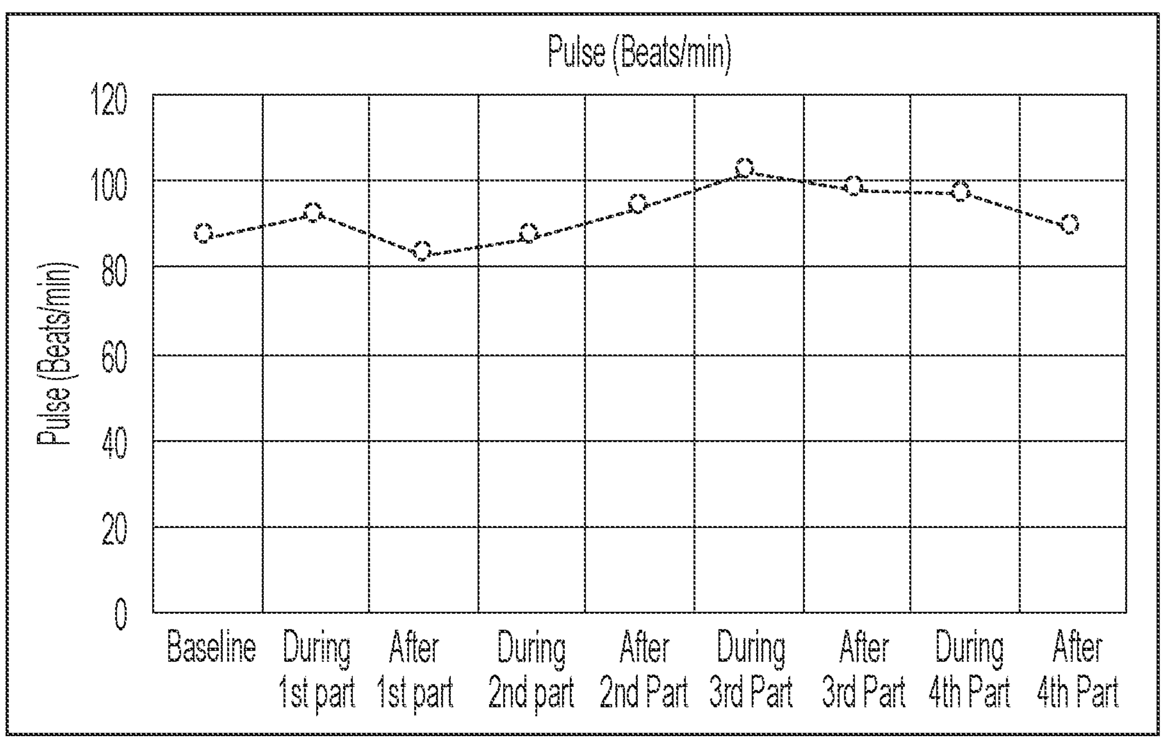
Figure 7A:
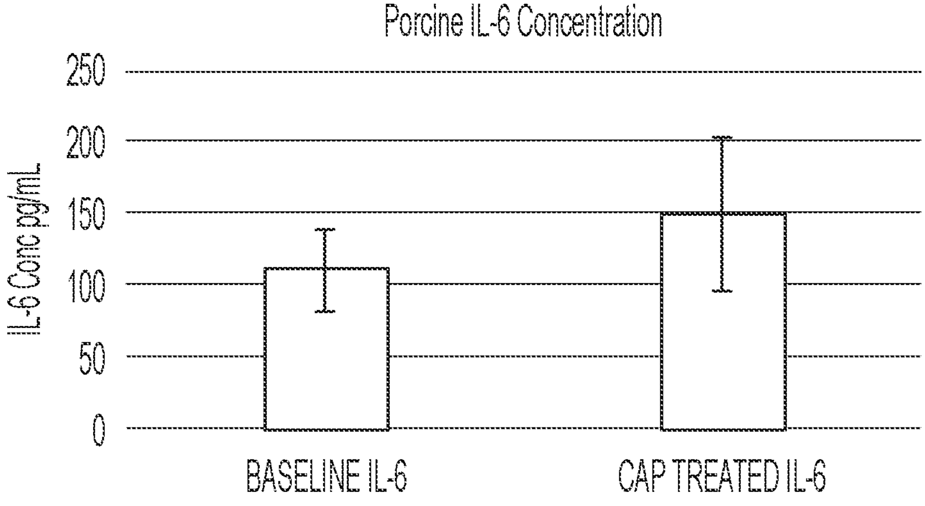
FIGS. 7A-7D are bar graphs of Detection of IL-6, TNF-α, CRP, Angiopoietin-1, post CAP treatment.
Figure 7B:
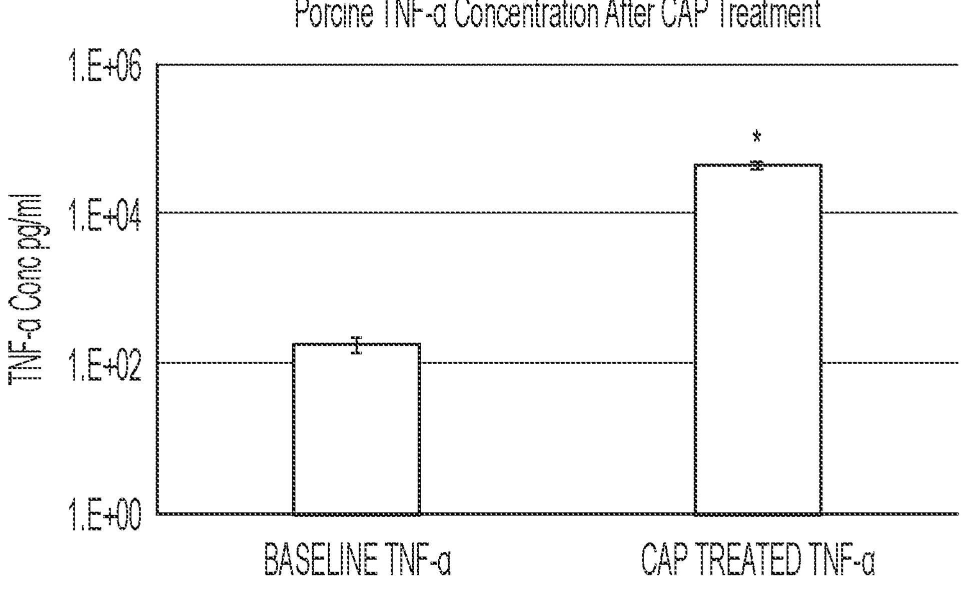
Figure 7C:
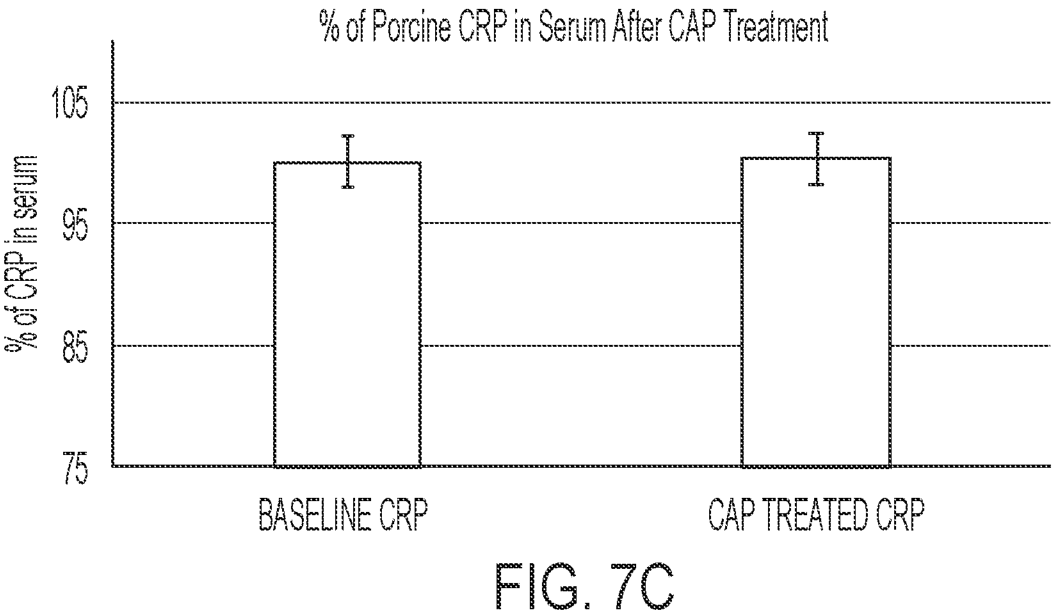
Figure 7D:
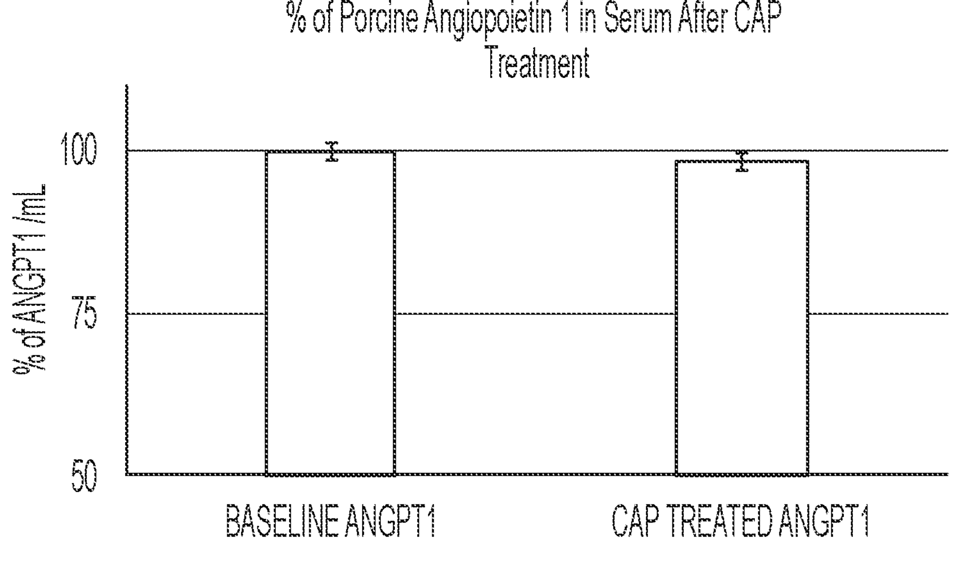

The setup for the experiment is shown in FIG. 4. A helium gas source 1110 is split into two lines 1112, 1114, with each of the two lines controlled by a mass flow controller (MFC) 1120. The Helium gas flow (50 to 1000 mL/min) in line 1112 is passed through an $H_2O$ filled container (Humidifier 1130*a*) and then fed into a mixing chamber 1140*a*. The helium gas flow in the line 1114 is fed directly into the mixing chamber 1140*a*. In this manner, with the mass flow controllers 1120 on the lines 1112, 1114 a relative $H_2O$ saturation in the gas exiting the chamber 1140*a* can be adjusted. Adjustment of the gas flow in the two lines 1112, 1114 makes the overall flow rate and humidity fine tuning of the gas flow exiting the chamber 1140*a* possible. The humidity may be in the range of 20%-100% with a preferred humidity of at least 70%. The total helium flow in this embodiment could be varied from 0.5 L/min to 5 L/min in all cases. The humidity of Helium gas in the chamber 1140*a* may be measured, for example, via calibrated High-Accuracy Humidity and Temperature Meter (not shown). The humidified helium gas from the chamber 1140*a* is fed into an electrosurgical generator 300, referred to herein as a "Cold Atmospheric Plasma (CAP) Generator." A variety of electrosurgical generators are known in the art and could be used with the present invention. The gas being fed into the Cold Atmospheric Plasma (CAP) Generator 300 is referred to herein as the "carrier gas."

At the same time, an un-humidified air supply 1150 (feed gas) is controlled by a mass flow controller (MFC) 1120. The air gas flow is passed through a second $H_2O$ filled container (Humidifier 1130*b*) and then is fed into a mixing chamber 1140*b*. Also at the same time, a source 1160 of an unhumidified pressurized third gas, oxygen in this case, is connected to a third $H_2O$ filled container (Humidifier 1130*c*). The humidified third gas (oxygen) is fed into chamber 1140*b* where it mixes with the humidified air. In this manner, with the mass flow controllers 1120 on the air and oxygen lines the relative oxygen percentage exiting the chamber 1140*b* can be adjusted. The humidity of each of the air and oxygen may be in the range of 20%-100% with a preferred humidity of at least 70%. The humidity of mixture in the chamber 1140*b* may be measured, for example, via a calibrated High-Accuracy Humidity and Temperature Meter (not shown) and the oxygen content may be measured for example with an oxygen sensor. The humidified air and oxygen from the chamber 1140*b* are provided to a respiratory delivery system 1170, such as a ventilator, CPAP machine, BIPAP machine, or other known respiratory deliver system. The respiratory delivery system 1170 will mix, adjust and measure the pressure, flowrate, ratio and frequency of the patient inbreath of exhaust air, oxygen and $CO_2$. The output of the respiratory delivery system 1170 is connected to the CAP joint mixer, for example, via tubing 1174 and connector 1176.

The output of the CAP generator 300 and the respiratory delivery system 1170 are connected to a dielectric barrier discharge (DBD) assembly 200, referred to herein as a "CAP joint mixer." A ground cable 1198 connects an outer electrode of the CAP joint mixer 200 to a ground in the CAP generator 300. While the grounding cable 1198 is shown separate from the tubing 1194 in FIG. 11, other arrangements are possible in which the ground cable 1198 is combined, for example, in a harness with the tubing 1194. Due to the presence of the $H_2O$, the ionization of Helium and $H_2O$ to $He^{+}+e^{-}$ chemical reaction will happen simultaneously. The cold plasma-generated reactive species (H2O2, NO2-, NO3-, ONOO—, and O2-) are produced.

The output of the CAP joint mixer 200 is connected to a delivery member 1190, which, for example, may be an endobronchial tube, oxygen CPAP (continuous positive airway pressure), BIPAP (Bilevel Positive Airway Pressure), ventilator face mask, or nasal $O_2$ cannula 1190 to deliver reactive species 1192, e.g., H2O2, NO2-, NO3-, ONOO—, and O2-, generated by the system into the patient's respiratory system.

Wu et al. (Wu, Y., et al., "*MS2 virus inactivation by atmospheric pressure cold plasma using different gas carriers and power levels*," Appl Environ Microbiol, 2015. 81(3): p. 996-1002) suggested that the ambient air as carrier gas produced the highest level of inactivation at power levels of 20 and 24 W, followed by the gas carriers Ar—$O_2$ (2%, vol/vol) and He—$O_2$ (2%, vol/vol). In addition, air is a required input gas for all ventilators. Hence air as carrier gas is a good option for a CAP-equipped ventilator. Relative humidity (RH) as an important factor of the air was studied for an optimal configuration in addition to CAP treatment parameters including discharge voltage (V) and treatment time (t). The feeding gas of Air/$O_2$ mixture and/or He was humidified by bubbling through water. The relative humidity (RH) of the humidified gases was measured constantly with a humidity sensor.

A total of 15 min treatment at 40 V was administered in 4+4+4+3 min manner with 5 min break between each partial treatment. During the treatment, vital signs of the swine including body temperature, End Tidal $CO_2$, $O_2$ saturation, blood pressure, and pulse were recorded in FIGS. 5A-5B and plotted in 6A-6D. Two tubes of 10 cc blood samples were collected in K2EDTA tubes before and 30 min after the CAP treatment.

Detection of IL-6, TNF-α, CRP, Angiopoietin-1, IL-1b & IL-10 by ELISA.

The induction of inflammatory cytokine responses upon CAP treatment has not been demonstrated before in Porcine or any other in vitro models. In this study, we investigated whether CAP treatment would induce cytokines in vivo injury to the tissues. We determined cytokine levels in serum samples taken from Porcine model 1 hour before and 6 hours after CAP treatment. To prevent stress-induced immunomodulation during blood sampling, the experimental animals was under anesthesia. The concentration of the cytokines IL-6, TNF-α, CRP, Angiopoietin-1, IL-1b & IL-10 were measured by ELISA method as described in the method section. TNF-α, was the only cytokine that should significant increase post CAP treatment compared to baseline control. IL-6, CRP and Angiopoietin-1 did not show any difference in the concentration between CAP treated and baseline samples (FIGS. 7A-7D). The cytokines IL-1b & IL-10 concentrations were below detection level. Statistical analysis was carried out by Mann-Whitney test. Unless otherwise noted, data were reported as a mean±SEM. Mann-Whitney test was used to evaluate the statistical significance of the results. Differences were considered significant at p values <0.05.

The structural preservation lung organ after CAP treatment was examined. Lung tissue integrity displayed high degree of homogeneity. Lung histology as well as ultrastructure was unaltered and well preserved. Lung parenchyma comprised well-inflated alveoli with slender alveolar septa and a continuous blood-air barrier with no signs of swelling or dissociation. Also, the surfactant system was unchanged. Peribronchovascular space, alveolar lumen, bronchiolar epithelium, bronchiolar lumen, alveolar septum and vascular lumen exhibiting no distortions after CAP treatment.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A system for sterilizing a flow of air in a ventilation system, comprising:

a source of a carrier gas;

a humidifier connected to said source of a carrier gas;

a feed gas inlet connected to said ventilation system;

an RF generator configured to generate an RF voltage to plasmatize said carrier gas into a plasma;

a mixer having an interior chamber, an active electrode inside said interior chamber and connected to an electrical output of said RF generator, an outer electrode connected to a ground and a dielectric barrier between said inner electrode and said outer electrode, wherein said mixer has a first fluid input port connected to said humidifier, a second fluid input connected to said source of a feed gas and a fluid output connected to a ventilation system; and a duct fan configured to draw said feed gas into said mixer.

2. A system for sterilizing a flow of air according to claim 1, further comprising a UV light array in said chamber of said mixer.

3. A system for sterilizing a flow of air according to claim 1, wherein said carrier gas comprises air.

4. A system for sterilizing a flow of air according to claim 1, wherein said feed gas comprises air.

5. A system for sterilizing a flow of air according to claim 1, wherein said RF generator is configured to operate with a frequency in the range of 10 kHz to 200 kHz and an output peak voltage in the range of 3 kV to 6 kV.

6. A system for sterilizing a flow of air according to claim 1, wherein said RF generator generates electrical energy having a frequency within 5 kHz of one of 40 kHz, 100 kHz and 200 kHz.

7. A system for sterilizing a flow of air according to claim 1, wherein said RF generator comprises a high frequency electrosurgical generator and a low frequency converter.

8. A system for sterilizing a flow of air according to claim 1, further comprising a duct connector to said mixer.

9. A system for sterilizing a flow of air according to claim 8, further comprising a compressor connected to said duct for supplying said carrier gas to said duct.

10. A system for sterilizing a flow of air according to claim 1, wherein said humidifier is configured to humidify said carrier gas to at least 70% humidity.

11. A system for sterilizing a flow of air according to claim 1, wherein said ventilation system is an air conditioning system.

12. A system for sterilizing a flow of air according to claim 1, wherein said ventilation system is heating system.

13. A method for sterilizing a flow of air in a ventilation system, comprising:

providing a flow of a carrier gas;

humidifying said flow of said carrier gas;

plasmatizing said humidified carrier gas with electrical energy from a RF generator in a mixer having an interior chamber, an active electrode inside said interior chamber and connected to an electrical output of said plasma generator, an outer electrode connected to a ground and a dielectric barrier between said inner electrode and said outer electrode, wherein said mixer has a first fluid input port connected to said source of a carrier gas, a second fluid input connected to said ventilation system at a first point and a fluid output connected to said ventilation system at a second point;

supplying a feed gas from said second fluid input into said mixer;

mixing said feed gas with said plasmatized carrier gas in said mixer; and supplying said mixed feed gas and plasmatized carrier gas to said ventilation system through said fluid output.

14. The method for sterilizing a flow of air in a ventilation system according to claim 13, wherein said step of humidifying said flow of said carrier gas comprises humidifying said carrier gas to at least 50% humidity.

15. The method for sterilizing a flow of air in a ventilation system according to claim 13, wherein said step of humidifying said flow of said carrier gas comprises humidifying said carrier gas to 100% humidity.

16. The method for sterilizing a flow of air in a ventilation system according to claim 13, wherein said carrier gas comprises air.

17. The method for sterilizing a flow of air in a ventilation system according to claim 13, wherein said feed gas comprises air.

18. The method for sterilizing a flow of air in a ventilation system according to claim 13, wherein step of supplying said feed gas to said mixer comprises drawing said feed gas into said mixer with a duct fan.

19. The method for sterilizing a flow of air in a ventilation system according to claim 13, wherein said step of humidifying said carrier gas comprises humidifying said carrier gas to at least 70% humidity.

* * * * *